United States Patent [19]
Shanbrom

[11] Patent Number: 5,811,471
[45] Date of Patent: Sep. 22, 1998

[54] DISINFECTANT PLASTIC SPONGE MATERIAL

[75] Inventor: Edward Shanbrom, Santa Ana, Calif.

[73] Assignee: Shanbrom Technologies LLC, Ojai, Calif.

[21] Appl. No.: 929,415

[22] Filed: Sep. 15, 1997

[51] Int. Cl.$^6$ .................................. C08J 9/28; C08J 9/40
[52] U.S. Cl. ............................................. 521/141; 521/149
[58] Field of Search ....................................... 521/141, 149

[56] References Cited

U.S. PATENT DOCUMENTS

| | | | |
|---|---|---|---|
| 3,912,666 | 10/1975 | Spitzer et al. | 521/72 |
| 3,912,667 | 10/1975 | Spitzer et al. | 521/65 |
| 4,422,877 | 12/1983 | Spitzer et al. | 521/79 |

Primary Examiner—Morton Foelak
Attorney, Agent, or Firm—Stefan J. Kirchanski; Graham & James

[57] ABSTRACT

A germicidal absorptive material for use in surgical packings, sanitary tampons and similar uses is provided by a sponge-like matrix of polyvinyl alcohol-acetal copolymer to which is tightly bound a germicidal disinfectant dye. Polyvinyl alcohol-acetal polymer shows exceptional avidity for a number of disinfectant dyes, both acidic and basic, such as methylene blue and gentian violet. Consequently, sponges of this material containing disinfectant dye release no dye to an aqueous solution The material is generally a porous matrix that releases no particles or fines into wounds or body orifices. Presence of bound disinfectant dye allows the sponge to inhibit bacterial growth in a number of different situations. Several common bacteria are killed by being incubated in the present of an embodiment of the invention which contains both methylene blue and gentian violet.

3 Claims, No Drawings

DISINFECTANT PLASTIC SPONGE MATERIAL

BACKGROUND OF THE INVENTION

1. Field of the Invention

The present invention is related to the medical products and personal care products and especially to germicidal bandage and sanitary napkin and tampon materials.

2. Description of Related Art

The importance of sterile techniques and especially sterile bandage material to modern medicine can hardly be overestimated. Almost every student of biology has heard the tales of how medical practitioners of not too long ago thought that pus and other signs of what is now known to be infection were essential to wound healing. These practitioners would reopen a wound that was not showing the expected pus and inflammation. This was changed by Lister's; discoveries regarding disinfection and the subsequent adoption of sterile bandage material for wound dressings. A continuing problem has been the propensity for microorganisms to grow in once sterile bandage material.

A major function of surgical bandages and packing materials is the absorption of various excreted fluids. These fluids are frequently rich in nutrients and are capable of supporting abundant bacterial growth. Since the surgical opening or skin surface is rarely absolutely free of bacteria, the bandage material soon supports a burgeoning bacterial population. These bacteria can easily cause serious infection and may also release a variety of harmful toxins. The obvious solution to such a problem is to change the bandage material often so that bacterial buildup does not occur. An additional answer is to treat the bandage material with some type of disinfectant to limit bacterial growth. Unfortunately, it has proven difficult to produce an effective disinfectant that does not readily wash out of the material, thereby greatly reducing its effectiveness and possibly causing irritation or damage to body tissues.

This problem is not limited to bandages, dressings or packings for wounds or surgical incisions. There are a number of instances where absorptive packings are placed in natural body orifices with significant possibility for dangerous bacterial growth. Various nasal packings can become bacterially laden following insertion into nasal passageways. Numerous deaths have resulted from "toxic shock syndrome" resulting from multiplication of *Staphylococcus aureus* bacteria in feminine care products, particularly tampons. There have been a large number of patents attempting to solve these and related problems. The reader's; attention is drawn to U.S. Pat. No. 5,641,503 to Brown-Skrobot which seeks to produce a germicidal tampon and contains a useful list of references to the toxic shock problem. A particular difficulty has been that many potent germicidal agents, e.g. iodine, are partially or totally ineffective in the presence of protein rich solutions such as blood or menses.

A large number of other inventors have labored to produce germicidal bandage and packing materials. U.S. Pat. No. 5,441,742 to Autant et al. discloses a modified cellulosic material with biocidal properties. Unfortunately, water releases the biocidal agents from the material with the concomitant problems of irritation or toxicity towards surrounding tissues. Iodine has been a favored biocidal material. Both U.S. Pat. No. 5,302,392 to Karakelle et al. and U.S. Pat. No. 5,236,703 to Usala rely on polymers containing polyvinylpyrollidone to bind and release iodine. Another approach is shown in U.S. Pat. No. 5,091,102 to Sheridan which relies on the presence of a cationic surfactant to provide germicidal properties to a dry fabric. All of these inventions suffer the problem of having a more or less toxic germicide that can leach from the material. What is needed is a germicide that remains in the bandage material where it can prevent bacterial growth without having any negative effects on living tissue.

OBJECTS AND SUMMARY OF THE INVENTION

Therefore, it is an object of the present invention to provide an absorbent material with germicidal properties for use in cleaning, bandages, surgical packings, sanitary napkins, tampons and other like devices which ideally absorb bodily fluids without supporting bacterial growth;

It is another objective of the present invention to provide a germicidal material that retains activity even in the present of blood and protein; and It is a further object of the current invention that the absorbent not release germicide to cause possible irritation to surrounding tissues.

These and additional objects that will become apparent to one of ordinary skill in the art upon reading the following specification are provided through the use of a sponge-like matrix of polyvinyl alcohol-acetal copolymer which contains a germicidal disinfectant dye. This polymer shows exceptional avidity for a number of disinfectant dyes and is capable of removing them from blood or other aqueous solutions. Consequently, sponges of this material treated with disinfectant dye release no dye to an aqueous solution The material is generally a porous matrix that releases no particles or fines into wounds or body orifices. Presence of bound disinfectant dye allows the sponge to inhibit bacterial growth in a number of different situations. This makes the invention ideal for any uses where bacteria-free absorbent material is needed.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of using polyvinyl alcohol-acetal copolymer containing disinfectant dye to provide a medical bandage or packing material or wipe that resists bacterial growth.

By "disinfectant dyes" is meant any of a number of organic dyes, generally known as "vital dyes," including methylene blue and related thionine dyes (electronegative or acidic), acridine orange, acridine yellow and related acriflavine (acridine) dyes (electropositive or basic), quinacrine and its derivatives, brilliant green, gentian violet, crystal violet and related triphenyl methane dyes (electropositive), and bis naphthalene dyes such as trypan blue and trypan red.

The cause of the disinfectant property of these dyes is not entirely known. Since many of the disinfectant dyes have oxidation-reduction (redox) potentials in the range of many electron transport components of oxidative metabolism, it seems possible that these dyes may operate by "short circuiting" electron transport pathways. Generally, the dyes show differential activity towards Gram-negative versus Gram-positive bacteria with electronegative (acidic) dyes being more effective on Gram-negative bacteria and electropositive (basic) dyes being more effective on Gram-positive bacteria such as *Staphylococcus aureus*.

The polyvinyl alcohol-acetal (PVA) is a copolymer of polyvinyl alcohol and formaldehyde (acetal) and may also contain polyvinyl acetate. The PVA preferred for use in the present invention is a medical grade of the polymer that is already widely used as surgical sponges and packings. It has a uniform pore size and releases neither fines nor solutes. This material. In the preferred material air spaces are introduced by foaming the material during polymerization. An unusual property of PVA is its ability to bind many electronegative as well as electropositive dyes. Most binding materials bind only negative or positive dyes and not both.

The antimicrobial material of the present invention is produced by binding an effective quantity of one or more disinfectant dyes to an appropriate PVA substrate. An "appropriate" substrate means PVA material with sufficient porosity and absorbency for a particular task. For example, simple bandages might best use a material that is quite porous and, hence, rather light weight and flexible as would be a cleansing wipe. Tampons, however, might best use a somewhat denser, highly absorbent grade of the material. The number and size of the air bubbles in the PVA material controls these properties. Properties required for a given application are well known to those of skill in the art. PVA is already used in nasal packings and other surgical packings. The same grade of PVA can be used for those applications with the current invention. "Effective quantity" means enough dye to inhibit bacterial growth over the projected period of use. Longer contact of the material with the human body will generally require a higher concentration of dye.

Generally, it is sufficient to soak the PVA material in an excess volume of dye solution followed by thorough washing to remove unbound dye. This process can be readily automated by checking the wash water spectrophotometrically to ensure complete removal of unbound dye. Initial experiments have applied the dye as an aqueous solution. Many of the disinfectant dyes are more soluble in ethanol than in water, but PVA is also somewhat soluble in ethanol so this solvent cannot be used. However, many disinfectant dyes are also quite soluble in glycerin. Therefore, treatment solutions containing 50% or more glycerin are very useful. The final wash solution can also advantageously contain a low percentage of glycerin (1 –2%) because a trace of glycerin left in the PVA can help maintain softness and improve future water uptake when the material is dried.

In one test 2 ×2 inch squares (one quarter inch thick) of PVA were saturated with a 4 mg/ml solution of gentian violet (C.I. Basic Violet 3), and unbound dye washed away after a 30 min binding period. The dyed PVA was then treated with a 2.0 ml of a suspension of either *Escherichia coli* or *Staphylococcus epidermidis*. After a 30 min incubation, the squares were squeezed out and the resulting liquid streaked on bacterial agar plates. After 24 hr incubation at 37 ° C. the plates were read. While the *E. coli* showed substantial growth, there was no bacterial growth in the *S. epidermidis* samples. This demonstrates the known result that basic dyes are more effective on Gram positive (Staphylococcus) than on Gram negative (Escherichia) bacteria. The significant point here is that while a goal of the present invention is to suppress bacterial growth, this experiment demonstrates actual bacterial killing.

A more realistic test of the present invention treated the 2×2 test squares with a mixture of both a basic (gentian violet) and an acidic (methylene blue) dye. The squares were treated with a stock solution containing 4 mg/ml of each of the two dyes. After washing, the squares were treated with 1.0 ml of bacterial growth medium containing either 100 cells of *E. coli* or *S. epidermidis*. The squares were incubated for 24 hr at 37 ° C. and then squeezed out. The resulting solution was serially diluted and plated out as before. As would be expected from the earlier experiment, all of the *S. epidermidis* cells were killed and no colonies grew up. Significantly, there were no colonies from the *E. coli* treatments either. Control material without the dyes showed abundant bacterial growth. Significantly the disinfectant dye mixture killed both Gram positive and Gram negative bacteria. The experiment was repeated with *Yersinia enterocolitica* (Gram negative), *Serratia marcesceus* (Gram negative) and *Staphylococcus aureus* (Gram positive), and again there were no viable bacteria following the treatment. Thus, a mixture of basic and acidic dyes bound to PVA prevents the growth of a wide variety of common bacteria. Repeating this experiment using blood or plasma as the bacterial growth medium gave similar results indicating that an important goal of this invention, i.e., germicidal activity in the presence of protein solutions, had been met. These experiments show that this material is ideal for a surgical absorbent material, a sanitary tampon to resist Toxic Shock Syndrome or a germicidal wipe for cleaning medical surfaces.

Both methylene blue and crystal violet have a long history of topical use. They are generally non-irritating, and preliminary experiments indicate that dyed PVA is also non-irritating. The unusual effectiveness of the present material is probably due to the binding of the dyes by PVA which prevent them from washing away and becoming diluted. The bound dye presents a very high local dye concentration that effectively eliminates bacteria. Presumably, the dye transfers from the PVA to the bacterial cells in contact with the dyed PVA. Even though dyed PVA appears non-irritating, there might be some concern that the disinfectant dye molecules could migrate to human tissue in contact with the material. This problem can be eliminated by providing a thin surface layer of undyed PVA (that is, untreated with disinfectant dyes; the material could well be colored with some safe and inactive dye of which many are known in the art)or some other permeable material to prevent direct contact between human tissues and the dyed material. In the case of some products like tampons a "clean" white product might be psychologically more acceptable. In such a case a thin envelop layer of white PVA or other material might be desirable.

Currently, PVA is the preferred binding material because it shows such a high avidity for the various disinfectant dyes—especially methylene blue and gentian violet. Other binding materials may be discovered with similar properties. The inventor has found that some types of polyurethane foam also are effective at binding the dyes. It is fairly easy to test materials for suitability in the present invention. Effective materials will become readily colored by the disinfectant dyes. Furthermore, extensive water washing will be unable to remove the tightly bound dye. The current invention has been described as including the step of treating the formed polymer with a dye solution. This is currently the preferred method of making the dyed polymer of the present invention although there is no reason that the dye could not be introduced during manufacture of the polymer, thereby simplifying the entire process.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A process for making an antimicrobial absorbent material comprising the steps of:

incubating a polyvinylalcohol-acetal sponge in a solution of disinfectant dye to bind the dye to the sponge;

washing the sponge to remove non-bound dye; and drying the sponge to form the antimicrobial absorbent material.

2. The process of claim 1, wherein the disinfectant dye is selected from the group consisting of methylene blue, acridine orange, gentian violet, brilliant green, acridine yellow, quinacrine, trypan blue, and trypan red.

3. The process of claim 2, wherein the disinfectant dye comprises methylene blue and gentian violet.

* * * * *